(12) United States Patent
Cavanagh et al.

(10) Patent No.: US 7,206,718 B2
(45) Date of Patent: Apr. 17, 2007

(54) METHOD FOR DESIGN AND MANUFACTURE OF INSOLES

(75) Inventors: Peter R. Cavanagh, 10300 Lakeshore Blvd., Bratenahl, OH (US) 44108; Jan S. Ulbrecht, Boalsburg, PA (US); Timothy B. Hurley, Boalsburg, PA (US); Huixiong Zhang, State College, PA (US)

(73) Assignees: DIApedic, L.L.C., State College, PA (US); Peter R. Cavanagh, Bratenahl, OH (US)

( * ) Notice: Subject to any disclaimer, the term of this patent is extended or adjusted under 35 U.S.C. 154(b) by 0 days.

(21) Appl. No.: 11/232,204

(22) Filed: Sep. 21, 2005

(65) Prior Publication Data

US 2006/0070260 A1    Apr. 6, 2006

Related U.S. Application Data

(60) Provisional application No. 60/611,775, filed on Sep. 21, 2004.

(51) Int. Cl.
*G06F 19/00* (2006.01)

(52) U.S. Cl. .......................................... 702/155; 705/1

(58) Field of Classification Search ................ 702/155, 702/167; 356/601; 382/100; 705/1
See application file for complete search history.

(56) References Cited

U.S. PATENT DOCUMENTS

| | | | |
|---|---|---|---|
| 4,235,027 A | 11/1980 | Singh | |
| 4,461,289 A | 7/1984 | Didier et al. | |
| 4,478,214 A | 10/1984 | Lamont | |
| 4,494,536 A | 1/1985 | Latenser | |
| 4,517,696 A | 5/1985 | Schartz | |
| 4,862,743 A | 9/1989 | Seitz | |
| 4,876,758 A | 10/1989 | Rolloff et al. | |
| 4,995,382 A | 2/1991 | Lang et al. | |
| 4,999,932 A | 3/1991 | Grim | |
| 5,078,128 A | 1/1992 | Grim et al. | |
| 5,088,503 A | 2/1992 | Seitz | |
| 5,098,421 A | 3/1992 | Zook | |
| 5,154,928 A | 10/1992 | Andrews | |
| 5,176,624 A | 1/1993 | Kuehnreich | |
| 5,197,942 A | 3/1993 | Brady | |
| 5,206,804 A | 4/1993 | Thies et al. | |

(Continued)

OTHER PUBLICATIONS

Cavanagh, et al., New Developments in the Biomechanics of the Diabetic Foot. Diabetes/Metabolism Research and Reviews, Oct. 23, 2000, pp. S6-S10, vol. 16-Issue S1, Wiley.

(Continued)

*Primary Examiner*—Edward Raymond

(57) ABSTRACT

A method for the design and production of improved pressure reducing therapeutic shoe insoles for a person. The method includes the steps of measuring a three dimensional image of a foot and the distribution of plantar pressures applied by a person's foot being measured for a pressure reducing insole. Selecting a shoe insole outline or template which best fits or corresponds to the shape of a foot being measured. A foot display is generated which combines and aligns the three dimensional foot shape and the plantar pressure distribution. A three dimensional insole display is generated which combines and aligns the foot shape and plantar pressure distribution, and includes modifications based upon selected pressure contour lines identified within the foot display which are above predetermined pressure thresholds.

16 Claims, 12 Drawing Sheets

U.S. PATENT DOCUMENTS

| | | |
|---|---|---|
| 5,237,520 A | 8/1993 | White |
| 5,298,013 A | 3/1994 | Lonardo |
| 5,329,705 A | 7/1994 | Grim et al. |
| 5,372,576 A | 12/1994 | Hicks |
| 5,378,223 A | 1/1995 | Grim et al. |
| 5,403,265 A | 4/1995 | Berguer et al. |
| 5,431,624 A | 7/1995 | Saxton et al. |
| 5,453,082 A | 9/1995 | Lamont |
| 5,483,757 A | 1/1996 | Frykberg |
| 5,571,077 A | 11/1996 | Klearman et al. |
| 5,609,570 A | 3/1997 | Lamont |
| 5,640,779 A | 6/1997 | Rolloff et al. |
| 5,642,096 A | 6/1997 | Leyerer et al. |
| 5,665,059 A | 9/1997 | Klearman et al. |
| 5,711,760 A | 1/1998 | Ibrahim et al. |
| 5,761,834 A | 6/1998 | Grim et al. |
| 5,768,803 A | 6/1998 | Levy |
| 5,769,801 A | 6/1998 | Tumey et al. |
| 5,778,565 A | 7/1998 | Holt et al. |
| 5,790,256 A | 8/1998 | Brown et al. |
| 5,797,862 A | 8/1998 | Lamont |
| 5,799,414 A | 9/1998 | Kellerman |
| 5,823,981 A | 10/1998 | Grim et al. |
| 5,829,171 A | 11/1998 | Weber et al. |
| 5,840,049 A | 11/1998 | Tumey et al. |
| 5,853,380 A | 12/1998 | Miller |
| 5,914,125 A | 6/1999 | Andrews et al. |
| 5,928,665 A | 7/1999 | Cercone |
| 5,929,332 A | 7/1999 | Brown |
| 5,931,797 A | 8/1999 | Tumey et al. |
| 5,973,221 A | 10/1999 | Collyer et al. |
| 6,000,082 A | 12/1999 | Nguyen |
| 6,082,025 A | 7/2000 | Bonk et al. |
| 6,083,185 A | 7/2000 | Lamont |
| 6,087,926 A | 7/2000 | Hajianpour |
| 6,092,310 A | 7/2000 | Schoesler |
| 6,127,026 A | 10/2000 | Bonk et al. |
| 6,135,116 A | 10/2000 | Vogel et al. |
| 6,141,889 A | 11/2000 | Baum |
| 6,205,230 B1 * | 3/2001 | Sundman et al. ............ 382/100 |
| 6,205,685 B1 | 3/2001 | Kellerman |
| 6,211,426 B1 | 4/2001 | Abrams |
| 6,228,044 B1 | 5/2001 | Jensen et al. |
| 6,324,698 B1 | 12/2001 | Freeman |
| 6,331,893 B1 * | 12/2001 | Brown et al. ................ 356/601 |
| 6,435,187 B1 | 8/2002 | Leithe et al. |
| 6,463,351 B1 | 10/2002 | Clynch |
| 6,464,659 B1 | 10/2002 | DeToro et al. |
| 6,468,237 B1 | 10/2002 | Lina |
| 6,481,120 B1 | 11/2002 | Xia et al. |
| 6,488,643 B1 | 12/2002 | Tumey et al. |
| 6,513,264 B2 | 2/2003 | Sinaie |
| 6,582,786 B1 | 6/2003 | Bonk et al. |
| 6,610,897 B2 | 8/2003 | Cavanagh et al. |
| 6,627,215 B1 | 9/2003 | Dale et al. |
| 6,643,956 B2 | 11/2003 | Mawusi |
| 6,653,520 B1 | 11/2003 | Mouton |
| 6,680,113 B1 | 1/2004 | Lucast et al. |
| 6,682,497 B2 | 1/2004 | Jensen et al. |
| 6,682,732 B1 | 1/2004 | Blake et al. |
| 6,696,433 B2 | 2/2004 | Ferguson et al. |
| 6,720,470 B2 | 4/2004 | Cavanagh et al. |
| 6,792,699 B2 | 9/2004 | Long et al. |
| 6,804,571 B2 | 10/2004 | Fullen et al. |
| 6,815,058 B2 | 11/2004 | Watanabe et al. |
| 2002/0032485 A1 | 3/2002 | Flam et al. |
| 2002/0095105 A1 | 7/2002 | Jensen |
| 2002/0133106 A1 | 9/2002 | Peled |
| 2002/0138923 A1 * | 10/2002 | Shaffeeullah ............. 12/142 N |
| 2003/0083604 A1 | 5/2003 | Stapf et al. |
| 2004/0133431 A1 * | 7/2004 | Udiljak et al. .................. 705/1 |

OTHER PUBLICATIONS

Royce Medical, Royce WoundCare Shoes and Insoles.

Bus, et al., Pressure relief and load redistrubution by custom-made insoles in diabethic patients with neuropathy and foot deformity, Clinical Biomechanics, Mar. 25, 2004, 10 p.

Fullen et al., In-shoe gait data dictate orthosis design, biomech, Mar. 2005, pp. 1-6, CMP Media, LLC, www.biomech.com.

\* cited by examiner

METHOD FOR DESIGN AND MANUFACTURE OF INSOLES

CROSS-REFERENCE TO RELATED APPLICATIONS

The present application claims priority from U.S. patent application Ser. No. 60/611,775 filed Sep. 21, 2004, the entire subject matter of which is incorporated herein by reference.

GOVERNMENT INTEREST

This invention was supported under National Institutes of Health grant no. 5 R44 DK 59074-02 awarded by the National Institute of Diabetes and Digestive and Kidney Diseases. The U.S. government has certain rights in the invention.

BACKGROUND OF THE INVENTION

1. Field of Invention

The present invention relates to insoles for footwear and more specifically to a method for computer aided design and manufacture of custom pressure reducing insoles for footwear.

2. Background of the Related Art

It is generally known that high plantar pressures under the foot can lead directly to undesirable injury and symptoms in the foot. Such injury or symptoms may include pain in a foot with sensation, or tissue damage and ulceration in a foot without sensation. As a result, reducing pressure at identified high pressure locations is believed to offer a therapeutic strategy for treatment of foot disorders.

In the past, insoles for footwear have been used to reduce pressure at presumed or identified high pressure locations. Custom and customized footwear insoles (where the term "custom" is used to mean both fully custom and modified off the shelf footwear insoles) are believed to provide improved pressure reduction over flat insoles and this has indeed been demonstrated by recent research. Manufacturing of such custom insoles is generally performed by trained pedorthists/orthopaedic shoemakers, who customarily use a negative mould of each foot for obtaining the desired base shape of the insole, to which they then make primarily subjective modifications to off-load the presumed or identified high pressure locations. Due to its subjective nature, this process has been shown to yield inconsistent results with respect to obtaining the desired pressure reduction and, because the process is labor intensive, it is expensive.

Computer aided manufacturing using numerically controlled machines is also possible, as disclosed in U.S. Pat. Nos. 5,088,503 and 6,804,571. Such systems have provided some of the measurements necessary to determine the high pressure locations to be accommodated within the insole to be designed. However, such systems have failed to provide the necessary combination of measurements to accurately align the high pressure locations or other locations of interest on the subject's foot with the insole to be designed and manufactured, in order to obtain precise and reproducible insoles from the measurements obtained. They have also not provided an approach to determining pressure regions and deciding the regions of interest based on a method of "thresholding" these regions based upon measured plantar pressure data. Such patented systems also suggest that footwear should reduce pressure distributions toward some ideal value but research has shown that the considerable variability in human feet makes such a concept untenable. The improvements provided by the present invention overcome these prior difficulties and result in an improved method and system for producing an improved pressure reducing insole.

SUMMARY OF THE INVENTION

The present invention provides an improved method and system for designing and manufacturing an improved pressure reducing insole for footwear of a person.

First, the three dimensional shape of the plantar surface of the person's foot is measured and stored, resulting in digital data in a three-dimensional reference frame. Such measurements may be made for a person within the offices of a foot practitioner or from an alternate location. A predetermined desired shoe insole template is also selected. The external shape of the insole template is also considered based upon the internal shape of the shoe in which the insole is to be used. The appropriate insole template is selected by comparing the two dimensional projection or foot shape from the measured three dimensional shape of a foot with an insole template, and selecting the template or outline data which best fits or matches with the measured shape of the foot, which is then aligned with respect to the template. The aligned three dimensional shape and the aligned insole template are stored for later reference.

The foot contact forces or plantar pressure distribution between the foot and the floor are also collected and stored during barefoot walking by measuring the distribution of foot forces applied by the person to a measuring arrangement. Foot pressures measured inside the shoe between the foot and a flat or other base insole could also be used. Again, such measurements may be made for a person within the offices of a foot practitioner or from an alternate location.

Once the necessary measurements are obtained, a combined foot display is then generated and stored by aligning the base insole, which is the measured shape of the foot appropriately oriented with respect to the insole template, together with the measured foot forces or plantar pressure distribution. Using this combined foot display, specific target areas or regions on the measured three dimensional shape of the foot (shown in two dimensions) are identified which have pressures above a predetermined pressure threshold of concern. Such pressure thresholds may be in the range of 150 kPa to 450 kPa or lower or higher, as may be selected. Additionally, such foot displays are generated at a manufacturing facility to which the necessary measurements have been communicated, either electronically or otherwise.

Once such high pressure regions or other target areas are identified and related to a location on the measured foot shape, the stored data provided by the foot display is in a format suitable to create modifications or customizations relative to the measured three dimensional foot shape which reduce the foot pressures where they are above the predetermined selected pressure threshold values. The pressure contour lines corresponding to the desired pressure threshold are used to form portions or all of the shape of the pressure reducing insole modifications, which may be either elevations or reliefs or both elevations and reliefs. The shapes generated with respect to the threshold pressure contour lines are stored as two dimensional polygons, and are combined with the three dimensional measured shape of the foot and insole template to generate a three dimensional insole display having the location of the desired modifications based upon the shape of the pressure threshold regions of the measured foot shape previously identified. Using the three dimensional display, features of the interventions may be specified, (such as intervention height or depth (z-value) and leading edge slope) where such modifications are based upon prior knowledge of pressure reductions typically obtained upon making such modifications.

Once the three dimensional insole display is generated, it is converted for use within the desired computer automated manufacturing equipment, with which the physical insole template is modified using the stored display data to create a pressure reducing insole. Specifically, the insole is modified to enable reduced plantar pressures in the target areas or regions identified. The pressure reduction modifications incorporated into the insole display may be obtained by creating reliefs or depressions (also referred to herein as "interventions") in the insole under the target area identified in the foot display. Alternatively, or in addition, an elevation can be created in the insole which is located adjacent to the target area identified. Such elevations serve to transfer load away from the part of the foot identified as being subject to elevated pressures. Regions of the foot that are distant from the target area—such as the medial longitudinal arch of the foot—may also be used for load transfer. Alternately, different materials may be incorporated into the insole template either immediately under the high pressure target area or adjacent to it.

It should be understood that the system, method, processes and procedures described herein could also be used for the production of custom made shoes in which some of the modification needed for pressure reduction are built into the mid-sole of the shoe underneath the insole. Additionally, it should be understood that modifications to the insole may be made which incorporate practitioner input relating to unique factors which are not otherwise accounted for in using the method outlined here.

These and other advantages and features of the invention will be better understood from the detailed description of an embodiment of the invention which is described in conjunction with the accompanying drawings.

DETAILED DESCRIPTION OF THE INVENTION

Figure 1:
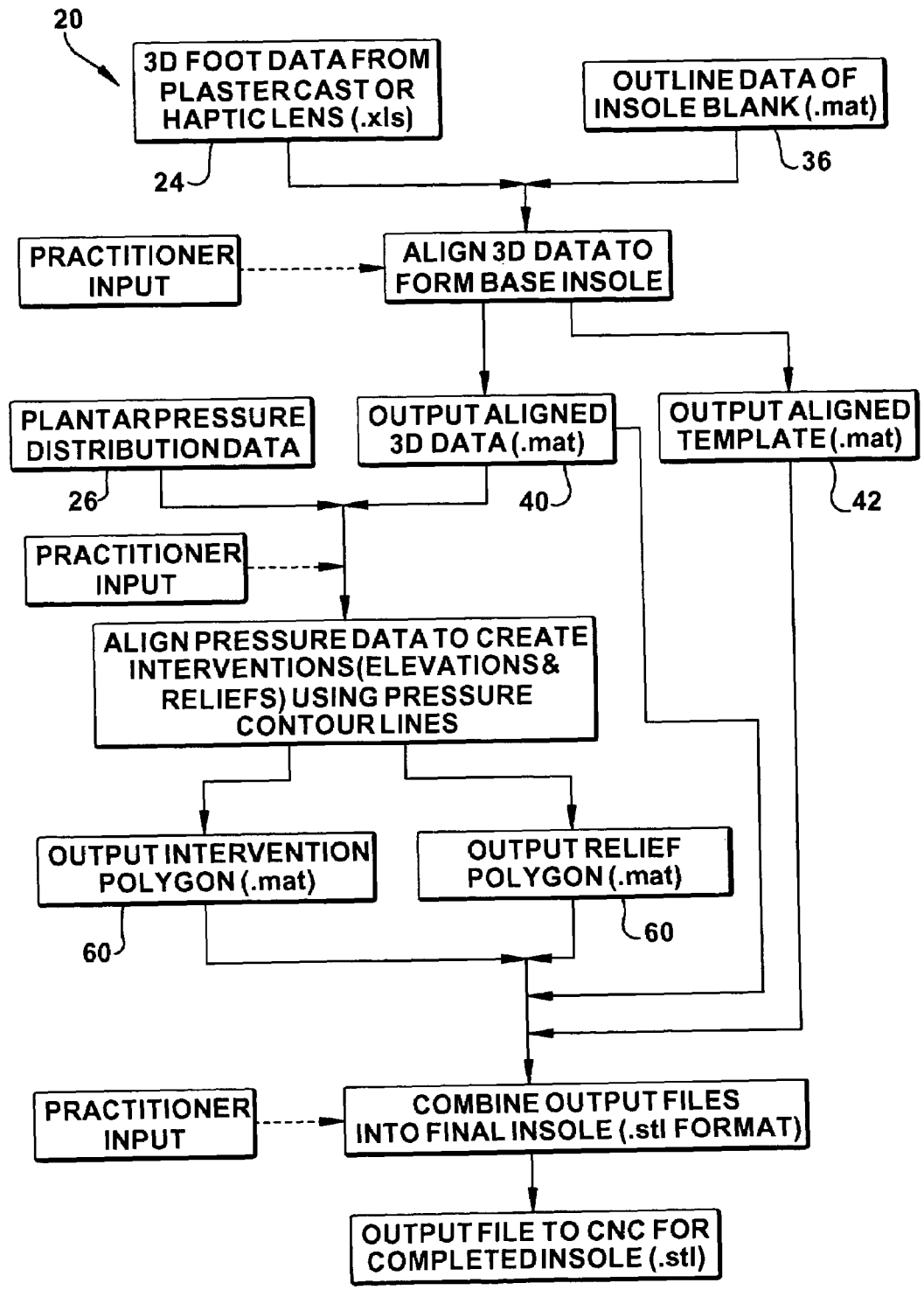
FIG. 1 is a schematic block diagram which provides an overview flow chart of the present method and system for manufacturing an improved custom pressure reducing insole.

FIG. 1 provides a schematic block diagram of an overview of the present method and system 20 for manufacturing an improved custom pressure reducing insole 22 using a computer aided design and manufacturing process. The method steps may be viewed as several separate operations, such as a data input operation, which may be performed at, or with the supervision of, a foot practitioner's office, and an insole processing or manufacturing process, which is performed within a manufacturing facility operation.

Figure 2:
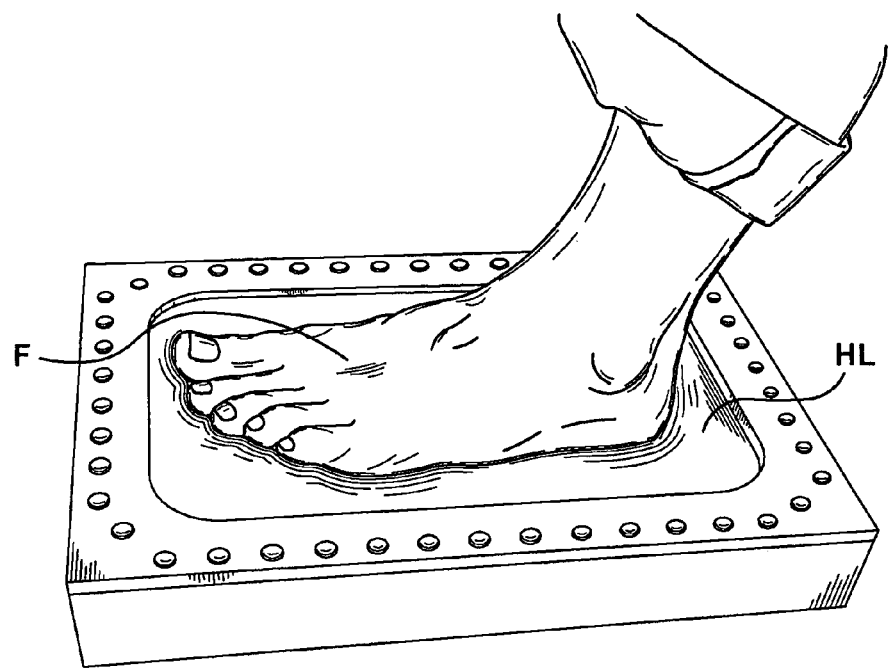
FIG. 2 illustrates the use of a haptic lens technology scanner for obtaining three dimensional foot data.
Figure 3:
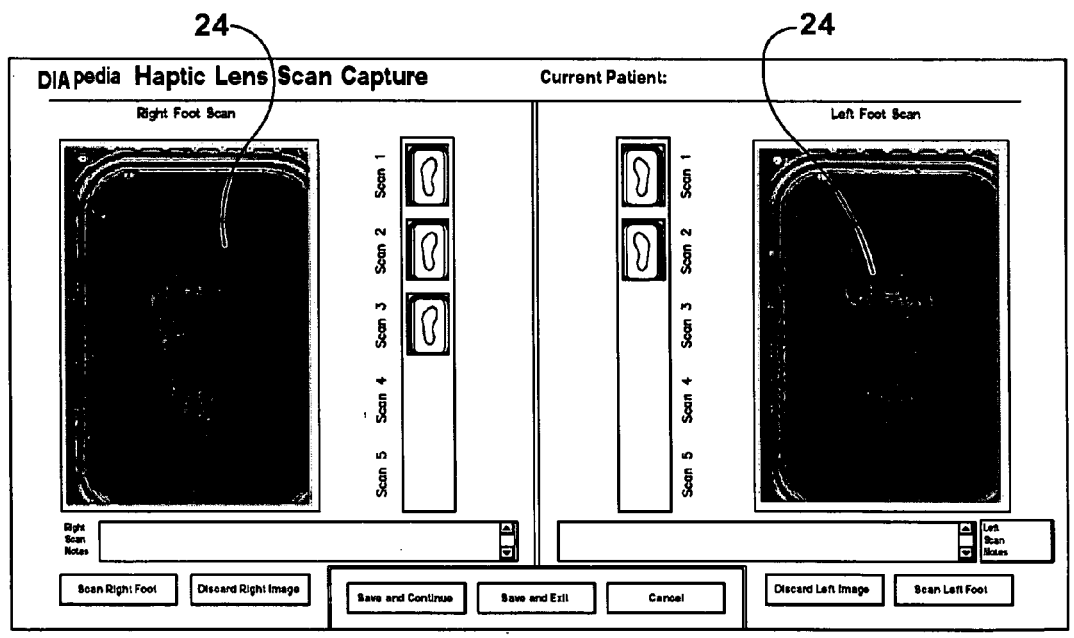
FIG. 3 schematically illustrates three dimensional foot data gathered using haptic lens technology of the type disclosed in FIG. 2.
Figure 4:
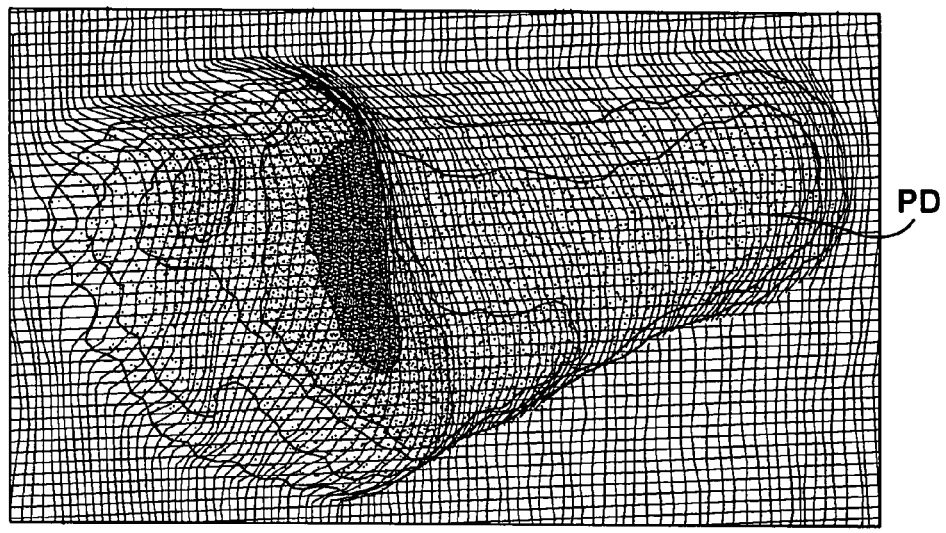
FIG. 4 schematically illustrates digitized three dimensional foot data obtained from plaster casts of a person's foot.

Data Input—the initial step of the present method is to collect relevant data from the person being measured for the pressure reducing insole. The measured data collected is a three dimensional scan of the foot 24 to assess three dimensional shape and obtain digital data in a three-dimensional reference frame. The three dimensional shape measured provides a baseline three dimensional shape for the insole. A barefoot pressure measurement 26 is also obtained, or may be provided by the measurement of in-shoe pressure during walking in a flat or neutral insole 28. Foot practitioner input may also be provided to supplement information regarding the person being measured. Additional data such as toe height measurement may also be obtained. Where such data is collected at a foot practricner's office, the data may be transmitted to the manufacturing facility via the internet and well known communication software as electronic data files. These data inputs are further described as follows:

Foot scans and profiles. Appropriate shoe selection and sizing is, an important consideration in the treatment of various foot-related conditions. Three-dimensional scanned images are used to measure the overall shape of a person's feet, as well as to obtain important two dimensional measurements such as an outline, length and width. Obtaining such foot geometry establishes a baseline insole for the person to which all subsequent modifications are applied. Haptic lens technology HL of the type disclosed in U.S. Pat. No. 5,459,329 and illustrated in FIGS. 2 and 3 may be used to collect and store such three dimensional data 24. Alternatively, plaster casts of a person's foot may be taken and digitized. Sample digitized data PD from a plaster cast is shown in FIG. 4. Additionally, other optical and contact digitizers are imaging techniques which may be employed to capture two and three-dimensional foot shape and profile.

Figure 5:
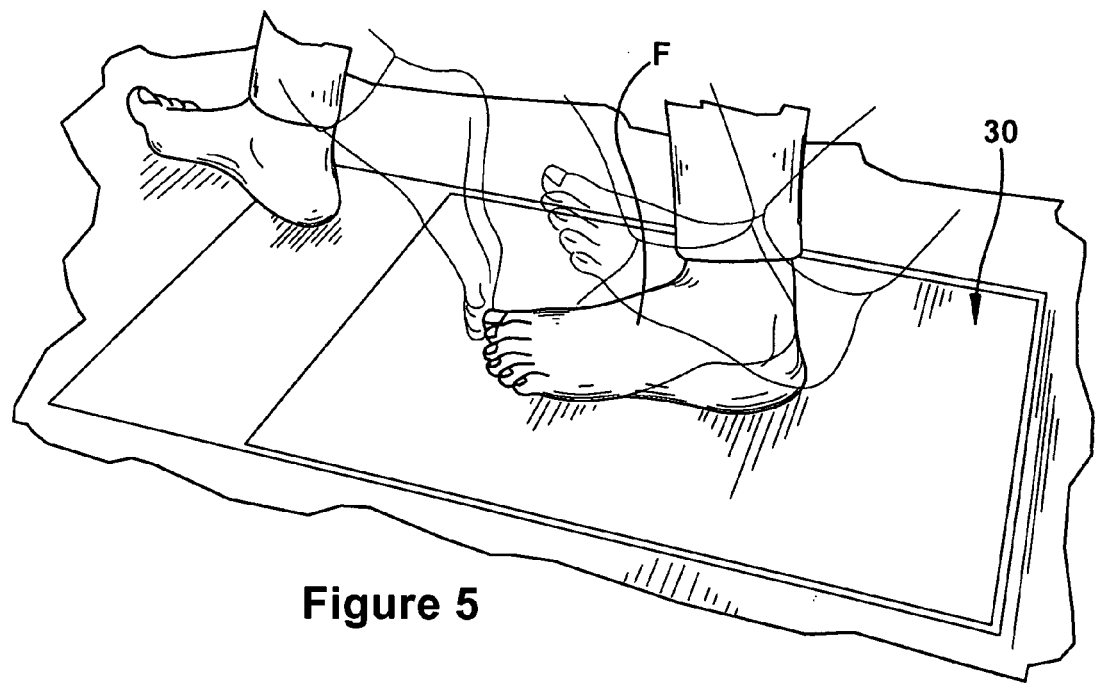
FIG. 5 schematically illustrates a prior art commercially available pressure platform system for collecting walking plantar pressure distribution data from a person's foot.
Figure 6:
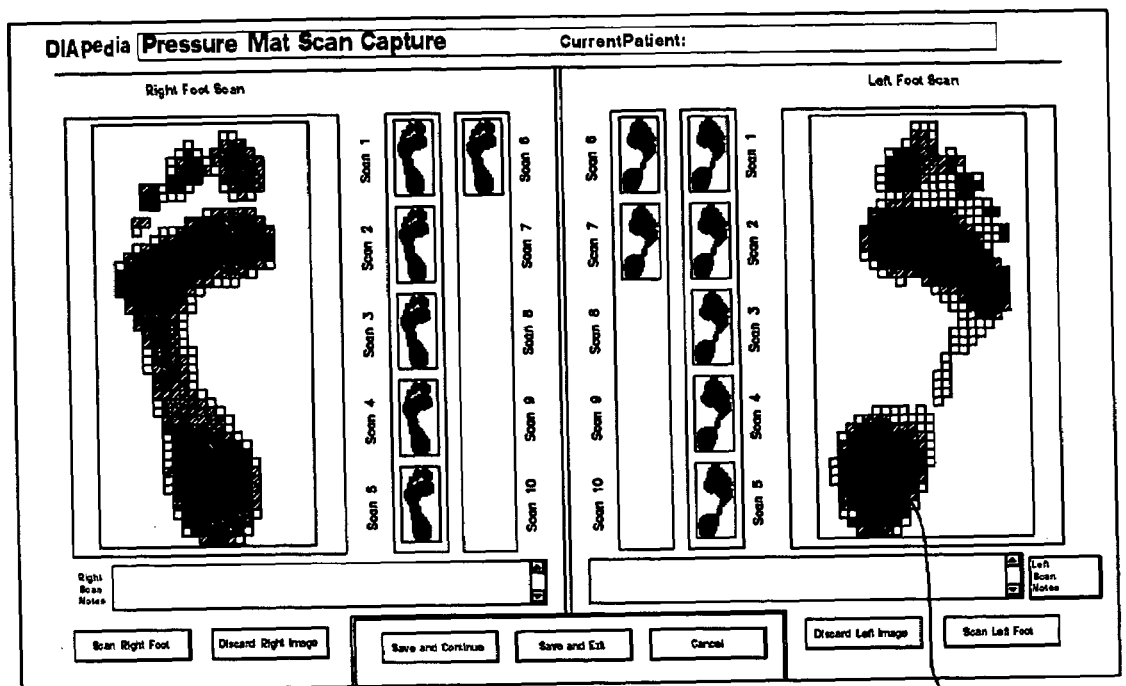
FIG. 6 schematically illustrates a computer screen image of EMED® data which shows a distribution of plantar pressure data collected from a person's foot, where each of the foot shapes includes discrete boxes containing the individually measured plantar pressure values applied at the indicated location by the person's foot to the pressure platform system as illustrated in FIG. 5 during walking.
Figure 7:
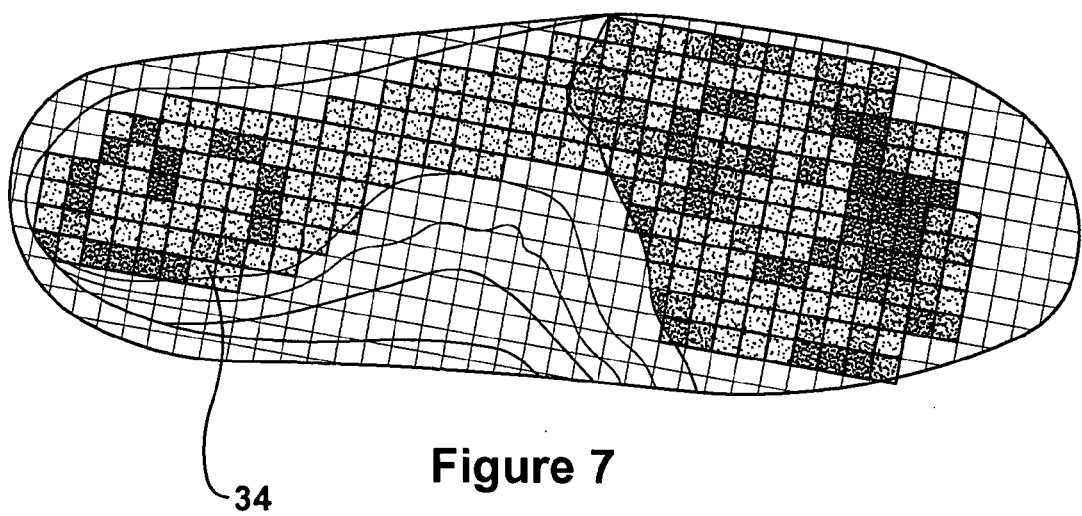
FIG. 7 schematically illustrates another representation of a distribution of plantar pressure data collected from a person's foot, where the foot shape includes discrete boxes, color-coded to indicate various pressure values applied at the indicated locations by a person's foot during walking, and pressure contour lines are superimposed over the discrete boxes to better illustrate the continuity of plantar pressures applied to the insole.
Figure 8:
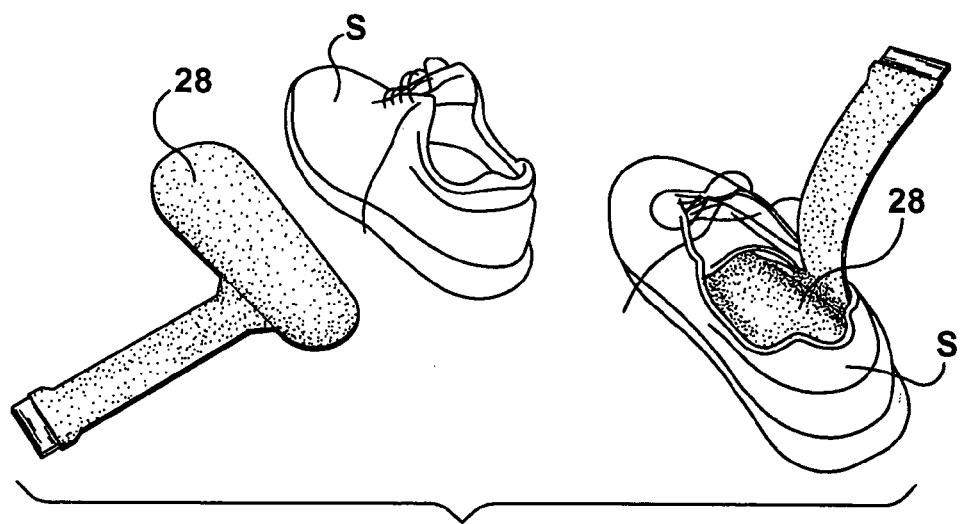
FIG. 8 illustrates a PEDAR® pressure insole for use in the measurement of insole pressure within a shoe.

Barefoot plantar pressure distributions. Plantar pressure distribution data 26 is collected using a pressure-measurement platform 30 which measures the barefoot pressure 26 of the person. As shown in FIG. 5, an EMED® system of the type available from Novel, GmbH of Munich, Germany may be used to obtain two dimensional plantar pressure distribution data 26 from a person being measured. The EMED system includes software which converts the measured data into a usable format thereby allowing for assessment of the plantar pressure data profile, as shown in FIG. 6. As shown, FIG. 6 illustrates a user interface screen showing measured foot images having individual boxes 32 indicating the pressure applied by the foot at each associated location during walking. FIG. 7 illustrates an alternative display of measured plantar pressure distribution which also includes pressure contour lines 34, which are overlaid on digitized three dimensional foot shape data 26. Colors (not shown in either FIG. 6 or 7), but commonly available with such software displays, are generally included in such images to more readily distinguish variations within the measured pressure data 26. Alternatively, barefoot plantar pressure 26 can be measured inside the shoe while the subjects walk in a conventional flat or base insole 28 having sensors for monitoring and collecting pressure data, and illustrated with a Novel PEDAR® insole measurement system in FIG. 8.

Foot practitioner input. The practitioner has an opportunity to provide input to the process by way of answers to questions describing the person's physical characteristics, limitations and personal lifestyle, and may impact insole design.

Toe height measurement. Sufficient shoe toe-box volume is important, particularly for people who suffer from foot deformities. Ample room in the toe-box will help to reduce the formation of new problems caused by contact of the shoe upper with the dorsum of the foot resulting from the use of an insole, which reduces overall toe-box volume. Any measurement of the height of anatomical features above the ground plane can be used for this purpose, and may impact the height or other features of the insole design.

Insole Template Selection. An insole outline 36 with an external shape which best corresponds to the shape of the foot F being measured, and which is appropriate for use within the footwear S to be worn by the person being measured, is also selected. Such insole outline data 36 may be selected from an electronic library of available templates or files which represent the outline or external shape of the insole to be created. The insole outline data 36 chosen from such stored data sets generally relates the measured foot length and width to a shoe/insole size. The selection of insole outline data may require assistance from the foot practitioner.

Insole Processing—Using the data collected from the steps above, which is communicated to an insole manufacturing facility as electronic data files, the custom insoles 22 are further designed and produced via the application of an integrated computer aided design—computer automated manufacturing (CAD-CAM) process. In the preferred embodiment, the present system and method makes use of the MATLAB® software program and associated tool sets, available from The Math Works, Inc. of Natick, Mass. at www.mathworks.com. The steps involved in this process are further detailed in FIG. 1.

Figure 9:
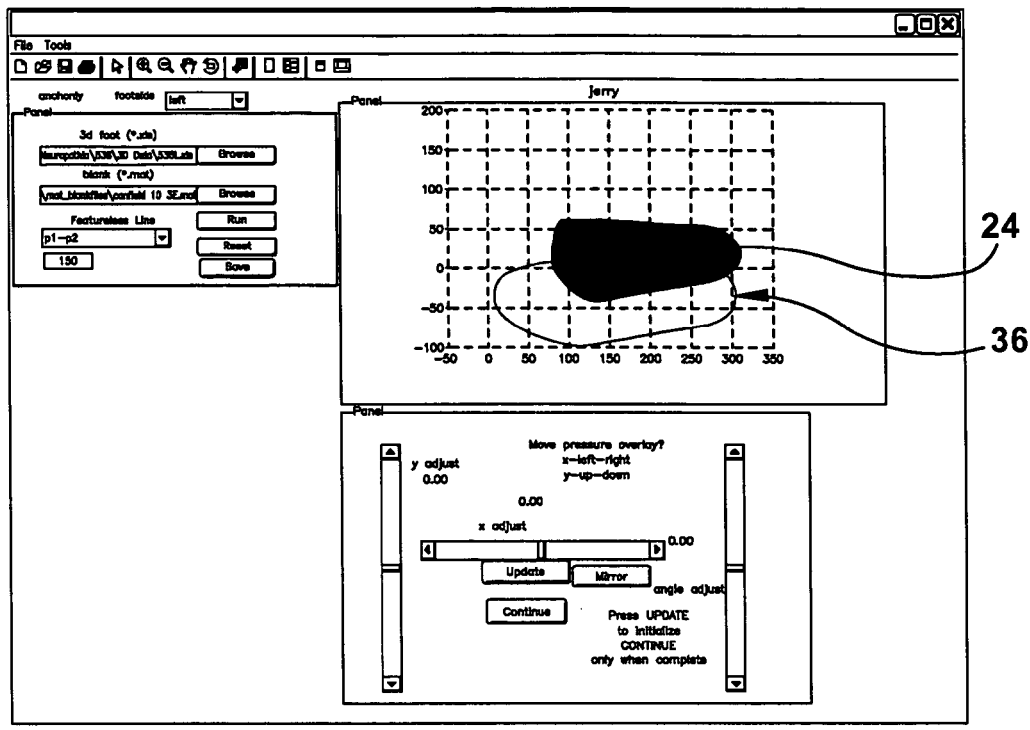
FIGS. 9 and 9A illustrate the foot shape data and insole outline data as a computer program screen image before and after alignment, respectively.
Figure 9A:
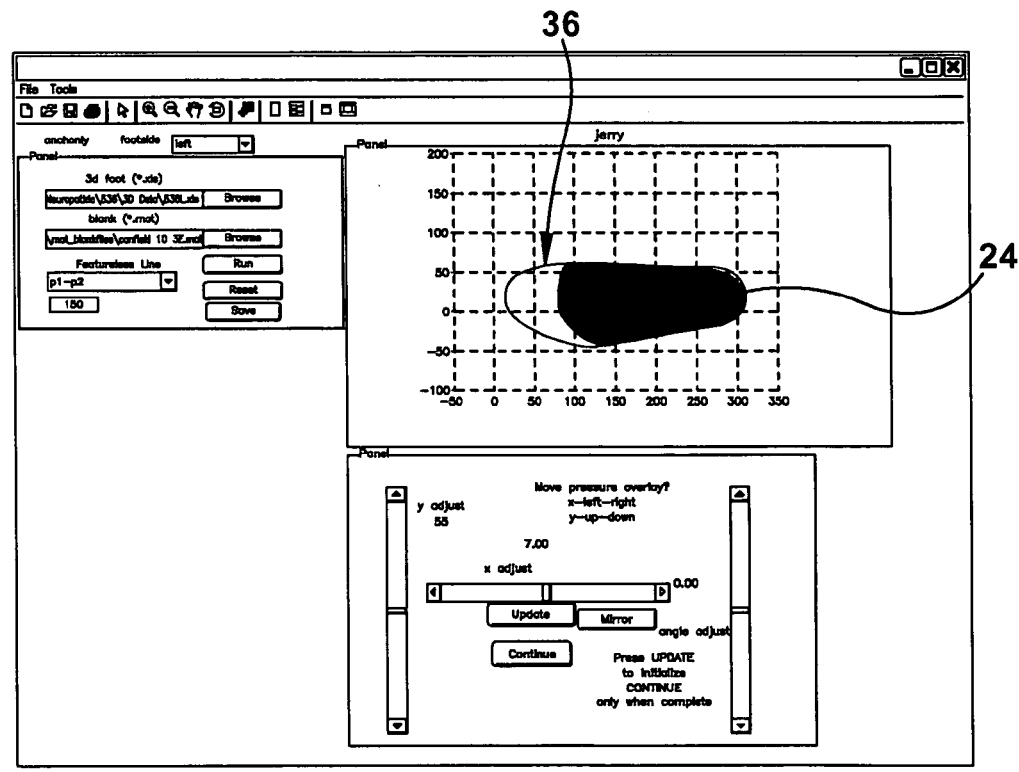
Figure 10:
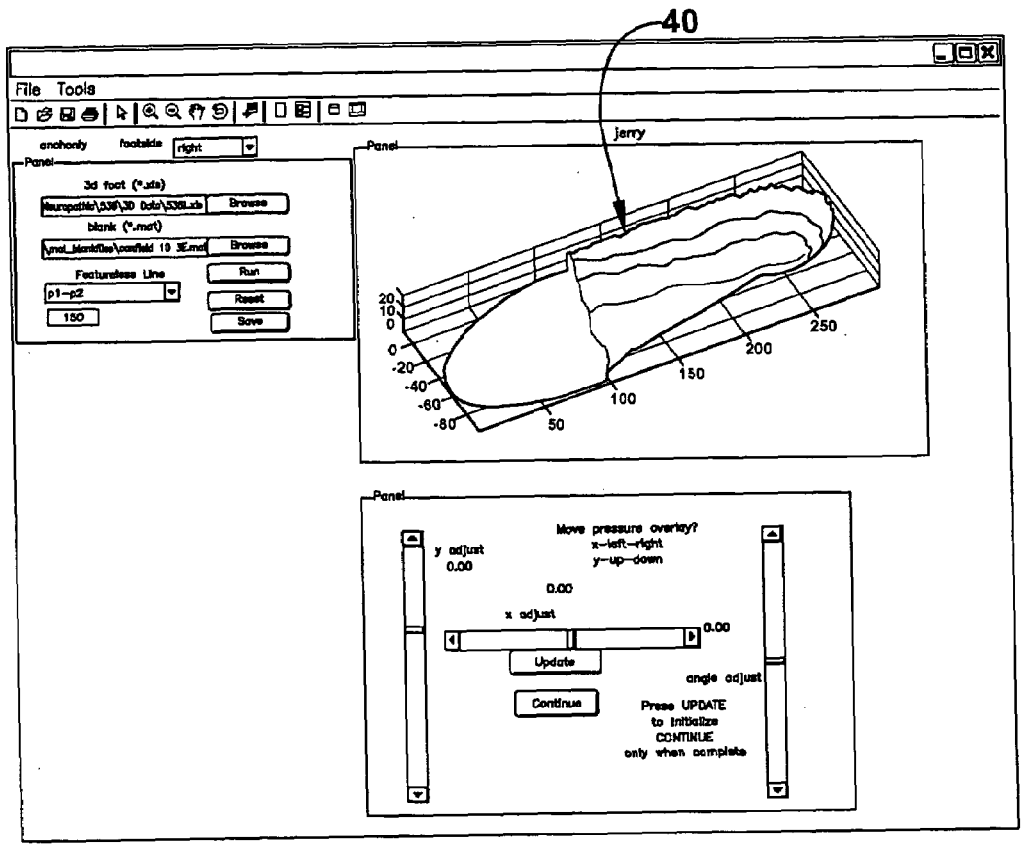
FIG. 10 illustrates a computer program screen image of the aligned three dimensional foot shape data or base insole.

Insole outline alignment with the foot shape. As shown in FIG. 9, the insole outline 36 or template previously selected is provided as an input to the computer design program. Additionally, the three dimensional foot shape data 24 is also provided. Both of these collected data files are illustrated in the computer program screen image of FIG. 9, but it is noted that the three dimensional foot shape data 24 is shown and used as a two dimensional image in this alignment step. Also, the foot shape data 24 in the toe region of the measured foot has been removed from the data set, such that the insole to be created addresses only modifications within the illustrated area of the foot shape. Once the data files are opened, the computer design program may be used to align the two dimensional foot shape image within the insole outline. The insole outline 36 is adjusted to a "best-fit" position with respect to the scanned foot image 24 by a series of translations and rotations (x, y and z axis adjustments are possible) based upon user input, as shown in FIG. 9A. Because the width of the foot is generally constrained inside a shoe to a value less than the barefoot width, it may be necessary to scale the foot shape and pressure data to allow appropriate fit within the insole outline 36. This can easily be done mathematically as a step in processing the shape and pressure distribution data, but small manual adjustments will always be necessary. The output data files generated from this alignment step for later processing include the three dimensional foot shape aligned within the specific reference frame of the insole outline (or having specific x, y, z coordinates), for example, as shown in FIG. 10 and also referred to as the "base insole" 40, and an insole outline also aligned with respect to the specific reference frame 42.

Figure 11:
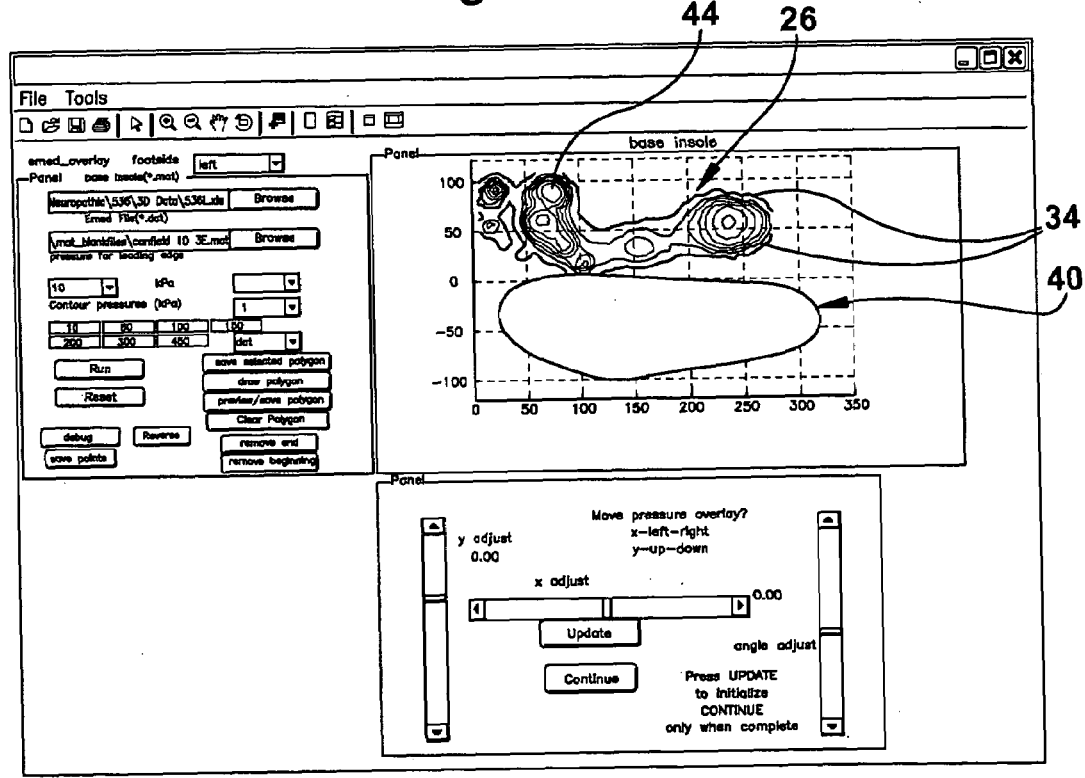
FIGS. 11 and 11A illustrate a computer program screen image of the foot display with the aligned three dimensional foot shape data, shown as a two dimensional view, and the measured plantar pressure distribution data, before and after alignment, respectively.
Figure 11A:
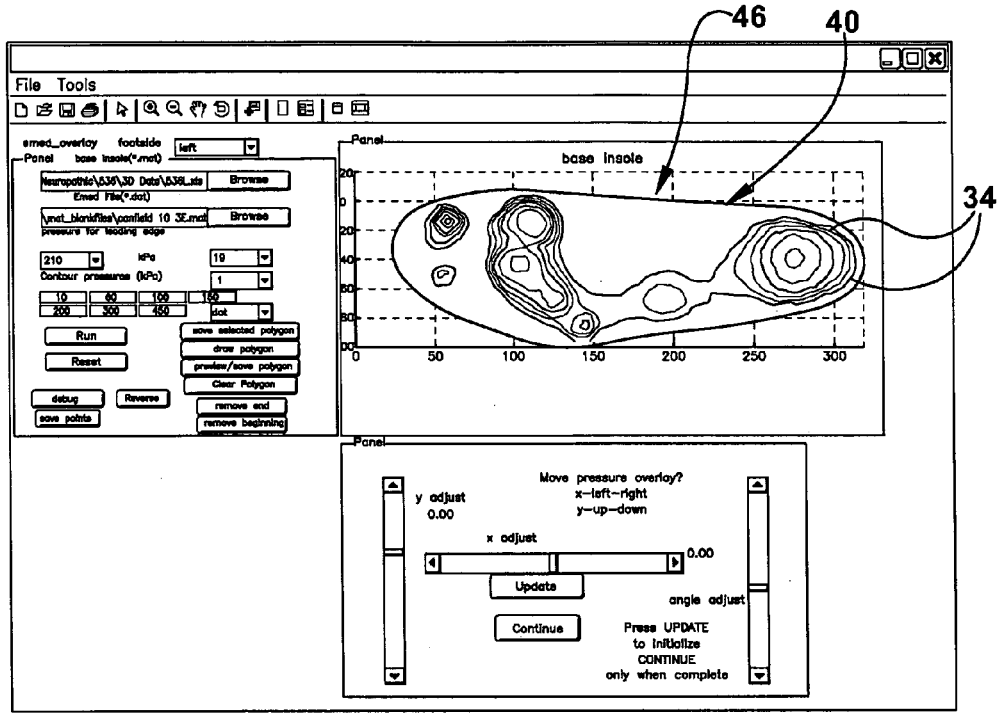

Superposition and thresholding of plantar pressure. The process of aligning the plantar pressure 26 on the base insole 40 is similar to the process of aligning the insole outline 36 as previously described. The measured barefoot plantar pressure data 26, expressed for each sensor of the pressure measurement device 30, are provided and displayed as a new two-dimensional foot image 44, shown in operator selected pressure contour lines 34 having the shape of a foot in FIG. 11. This pressure distribution 26 is adjusted to a 'best-fit' position over the aligned three dimensional base insole 40 (shown in FIG. 11 as a two dimensional image) by a series of translations and rotations (x, y and z axis adjustments are possible) based upon user input. Features in the pressure distribution such as toe pressures and the center of the heel distribution are useful for this purpose. An automatic algorithm can be implemented for this purpose, but small manual adjustments will always be necessary. Once the plantar pressure distribution 26 is aligned with the three dimensional foot shape data 24, this aligned data or "foot display" 46 is stored as shown in FIG. 11A.

Figure 12:
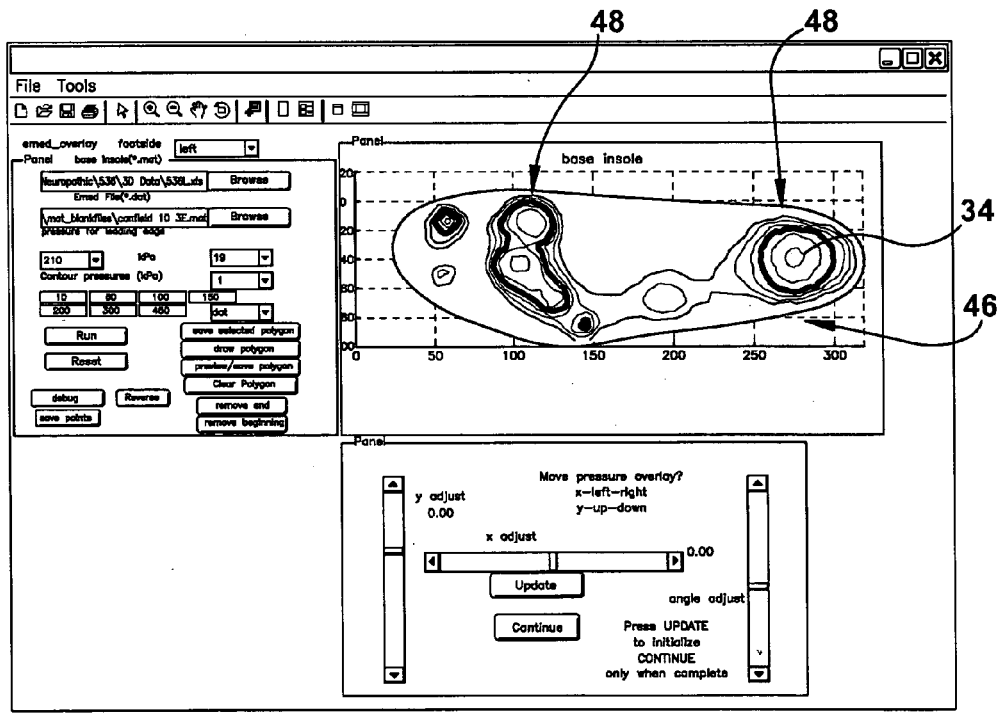
FIG. 12 illustrates a computer program screen image of the highlighted threshold pressure contour lines within the three dimensional foot shape data with measured plantar pressure distribution data.

Once the positioning is finished, individual measured pressure values are compared to a threshold pressure value, which is established by the user/operator, and a region of pressure distribution is identified and highlighted within the computer program as shown in FIG. 12 at 48. In the illustration of FIG. 12 the highlighted pressure contour lines 48 selected are 210 kPa, such that pressure sensor values that exceeded the threshold pressure value may be located within or outside the highlighted contour line 48. In the preferred pressure reducing insole 22 embodiment of the present application, the identified threshold pressure regions are used to form the shape of the insole modifications or interventions to be made. In the preferred embodiment, threshold pressures of approximately 200 kPa, when measured using a sensor array with resolution of approximately 2–8 sensors per $cm^2$, are believed effective for the location and geometry of modifications or interventions to be made to the improved pressure reducing insole 22 of the present application. As used herein, the term interventions or modifications may include either elevations or reliefs, including depressions and openings, or combinations of both elevations and reliefs.

Figure 13:
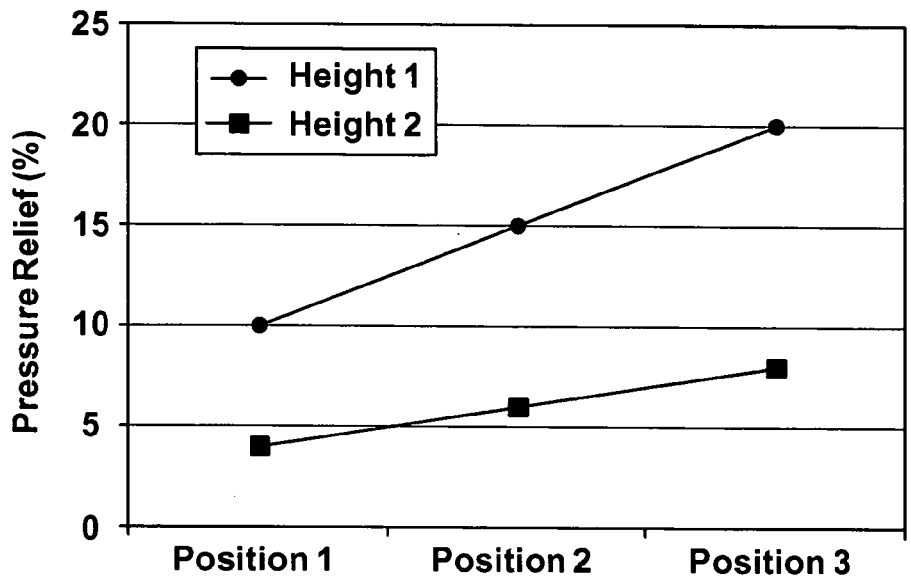
FIG. 13 schematically illustrates the relationship between intervention feature position and intervention feature height on pressure reduction under a metatarsal head.

Intervention Feature Geometry and Position. Insole modification features are specified based on rules derived from the results of empirical studies on human subjects or the results of finite element modeling studies. An example of the former is the relationship between the location and magnitude of peak pressure at a prominent metatarsal head and the location and height of a pressure relieving feature placed posterior to this region. Such a relationship is shown schematically in FIG. 13. Depending on the required pressure relief, the choice of feature characteristics can be made algorithmically. Features may include various surface elevations and/or depressions and/or variations in the material used, each aimed at transferring load away from high pressure areas to lower pressure regions of the plantar surface.

Figure 14:
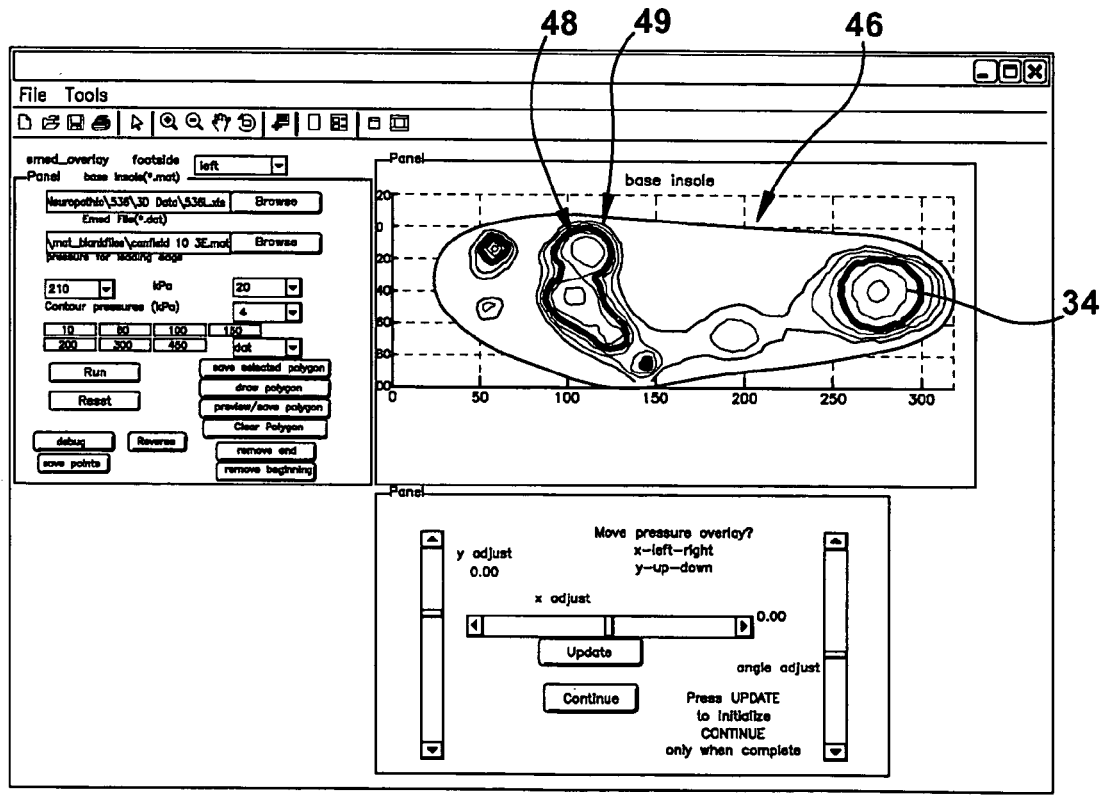
FIG. 14 illustrates a computer program screen image of the highlighted threshold pressure contour lines within the three dimensional foot shape data with measured plantar pressure distribution data, and with a selected portion of a contour line highlighted which may form the leading edge of an insole intervention.

In the illustrated embodiment, an intervention such as an elevation is formed using the threshold pressure contour line 48 previously highlighted in FIG. 12. Once the desired threshold pressure contour lines are identified, the desired region meeting this threshold is selected for creation of a modification. In the FIG. 12 illustration, for example, the highlighted bilobal shaped pressure region generally under the metatarsal head of the foot could be selected using the computer program. Once selected, the specific portion 49 of the highlighted threshold pressure contour line 48 which will form at least a portion of the shape of the modification or intervention may also be selected. As shown in FIG. 14, a posterior edge portion 49, indicated by a dashed line, on the threshold pressure contour line 48 has been selected to form the leading edge 52 of an elevation intervention 50. To the extent the selected threshold pressure contour lines 34 are disconnected but adjacent, connections between the adjacent lines are selected to form the highlighted region. The computer program may also be used to manually remove any end or beginning points of the contour line, so that the desired shape of the leading edge 52 for the intervention 50 is obtained. It is noted that in the anterior insole direction from the leading edge, the foot data 24 is featureless in the illustrated embodiment. The nature of the featureless line created ahead of the leading edge 52 may require blending of the data so the intervention being created blends with the three dimensional base insole 40. Such blending may be accomplished by performing a one dimensional interpolation in the x axis direction.

Figure 15:
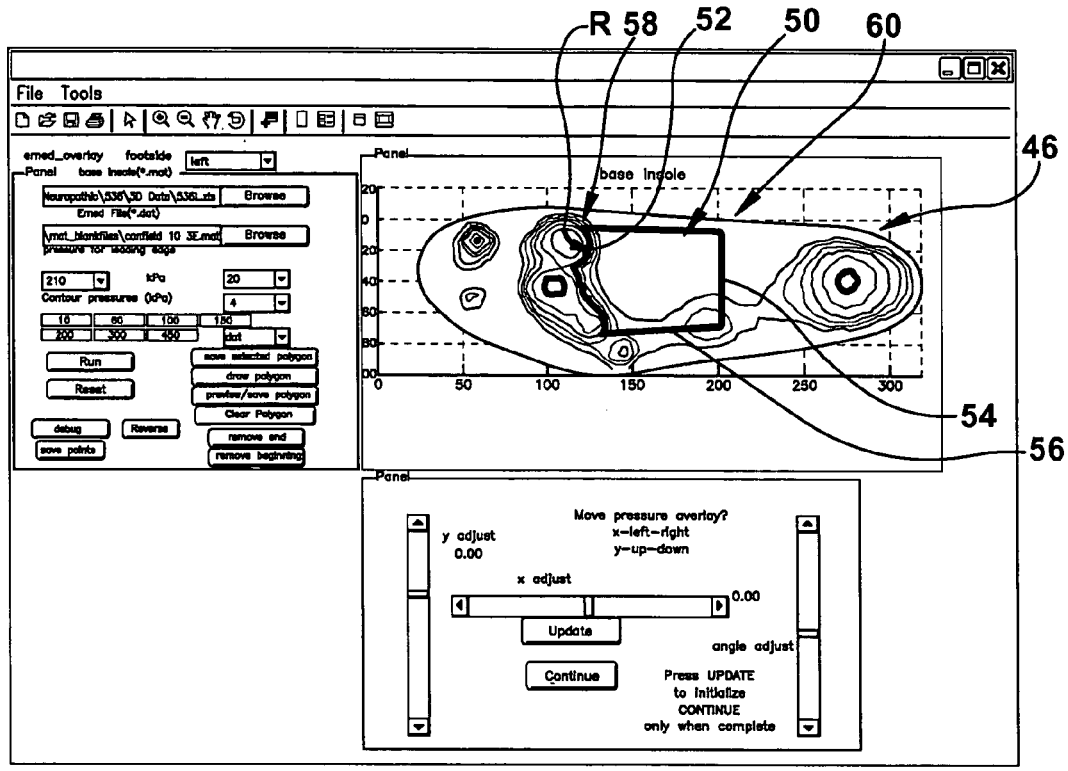
FIG. 15 illustrates a computer program screen image of the polygonal shaped intervention formed using the threshold pressure contour line from the three dimensional foot shape data with measured plantar pressure distribution data to form the leading edge thereof.

The one dimensional shape of the intervention 50 may then be completed as desired and saved as a data file. In the illustrated embodiment, the tail point or rear edge 54 of the shape of the intervention 50 is selected at a location which is generally one third of the overall length of the foot, or approximately 8–10 cm for a base insole of 25–35 cm, and straight side edges 56 are formed from the end points 58 of the leading edge contour line 49 to the tail point 54 selected, resulting in a polygon as illustrated in FIG. 15.

Once the desired intervention 50 shape is obtained, the shape is saved as a data file. Additional elevations or reliefs 50 may also be created for inclusion within the insole 22. For example, a relief or depression having a shape of the region of the threshold pressure contour 48 identified at 300 kPa, as illustrated by the polygon R in FIG. 15, could also be selected and saved as a data file.

Figure 16:
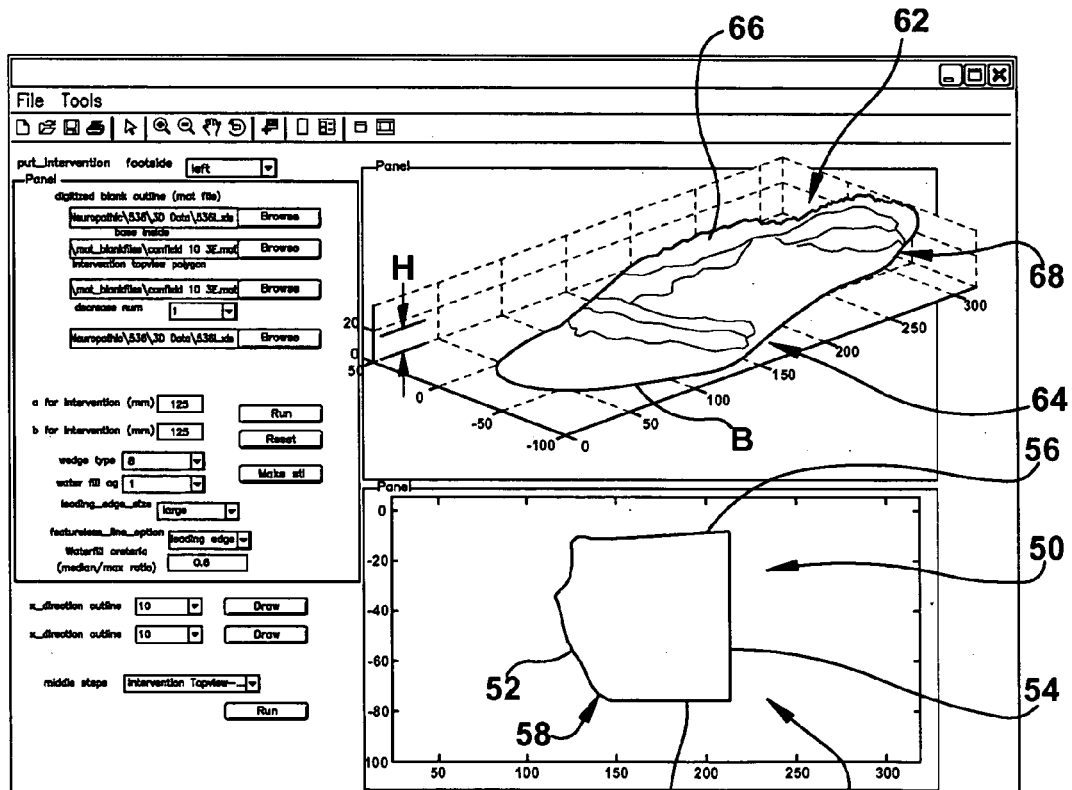
FIG. 16 illustrates a computer program screen image of the three dimensional insole display generated, together with a smoothed shape of the intervention having the threshold pressure contour line forming the leading edge.

The interventions 50 are then incorporated with the aligned base insole 40 and the aligned outline or template 42 into a three dimensional insole display 62 shown in FIG. 16. As shown in FIG. 1, the aligned outline or template, aligned three dimensional foot shape data 40 or base insole, and the intervention polygon files 60 created, if any, are selected within the computer program for incorporation into an insole display 62. The height of the intervention and distance back (and thus, slope) from the leading edge 52 of the intervention 50 are also selected. In the preferred and illustrated embodiment, a height H of approximately 12.5 mm above a base B, which is approximately 5–6 mm, is believed to provide desired pressure reductions during use of the insole. A slope from the leading edge of the intervention toward the tail point edge 54 is preferably within the range of 30 to 60 degrees, and more preferably approximately 45 degrees, to obtain desired pressure reductions during use of the insole 22. Once the dimensional features of the intervention 50 are defined, various methods may be employed to combine the intervention with the three dimensional surface of the base insole 40. With these characteristics and dimensions, the intervention 50 effectively blends into the three dimensional foot shape 24. To ensure a uniform surface along the edges of the intervention 50 with a border 64 of the base insole 40, additional blending may be required. Such blending may be determined based upon the shape of the area between the intervention edges 56 and the border, and values such as either the maximum or median values of the edge 56 or the border 64 data may be used to obtain the desired blended surface 66 result.

It will be understood by one of ordinary skill in the art that the creation of additional elevations may proceed using these same procedures. Likewise, the creation of reliefs is generally formed by selection of an entire threshold pressure contour line 48, or a full circular shape, for example, under the metatarsal head region in the illustration of FIG. 14. The depth of such a relief or depression is preferably in the range of approximately 1 to 3 mm from the base B of the base insole 40.

Smoothing algorithms, such as low and high pass filters, may be selected to clean rough edges of the insole display 62. For example, where data points in the heel cup section are inconsistent, filling may be required to bring all data points to the highest existing data point. Additional smoothing algorithms to blend the shape of the intervention with the three dimensional foot shape may also be required as discussed above. After final data adjustments are complete, the modified insole surface is smoothed and regenerated. The final smoothing of the entire insole surface data is done, for example, using the spline tool feature within the MATLAB computer program. The modified insole data is then saved to enable recreation of the identical insole for a person at a later time.

The final insole 22 is then created within MATLAB as shown in FIG. 1 by combining the data indicated, which is then displayed as an insole. If the insole display 62 requires further revisions, additional changes may be made. Once a final insole display 62 is satisfactory, the computer design program converts the mat two dimensional data files and other three dimensional foot shape data files into a stereolithography file (.stl), which is of the type which generates a tool path in the convention appropriate for a specific computer controlled milling or CNC machine in machine readable numeric code to create the actual physical insole.

Figure 17:
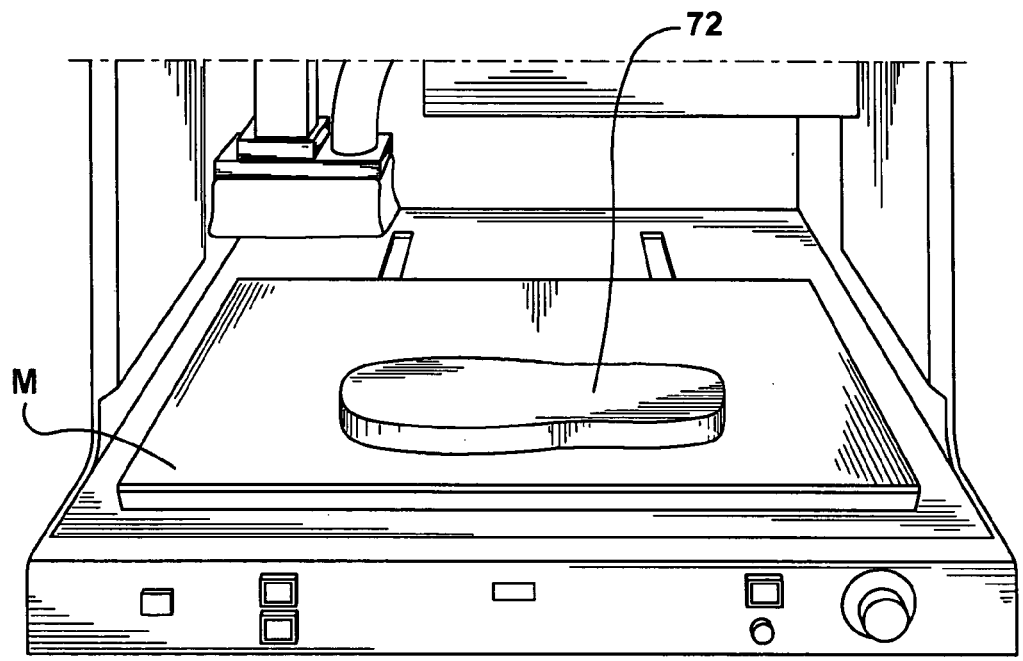
FIG. 17 illustrates the blank insole template to be milled to the modified insole within a computer controlled milling machine.

Milling the insole. The tool path file is transferred to a computer controlled machine M as shown in FIG. 17. The milling machine M directs the fabrication of the pressure reducing insole starting from a blank stock 72 of a suitable foam material, preferably ethylene vinyl acetate having an initial thickness of 1 to 2 inches, and a Shore A hardness within a range of 15–60, more preferably 35–45, and more specifically approximately 40, such as Cloud EVA Foam supplied by PEL Supply Company of Cleveland, Ohio.

Figure 18:
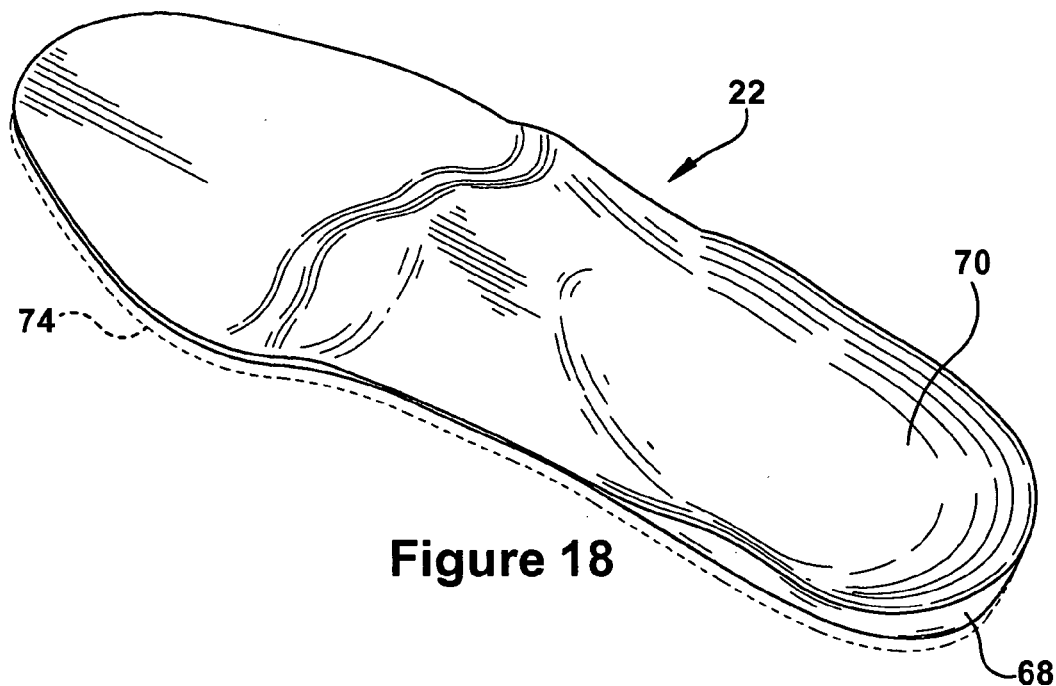
FIG. 18 illustrates a final modified pressure reducing insole manufactured in accordance with the methods, processes and system of the present application.

The finished insole. As shown in FIG. 18, the custom milled insole 22 produced is hand finished, which may include fine grinding and lamination of a top cushioning layer 70. The cushioning layer 70 is preferably of a 5 mm or less thickness, and of a polyurethane foam, which may include a fabric lining, having a Shore A hardness within a range of 5–55, and more preferably approximately 15, such as Poron® performance medical grade manufactured by Rogers Corp. Prior to application of a top cushioning layer, it may be desired to add a resilient, flexible elastomeric material within any reliefs, in order to provide additional cushioning between the foot and the footwear. Such elastomeric material 74, shown in phantom under the top cushioning layer in FIG. 18, may be a silicone gel material, such as G.E. RTV 6136 silicone gel, of the type available from G.E. Plastics. The volume of gel required for the relief may be simply calculated by creating and counting a 1×1 mm grid size formed from the polygonal shape of the relief which is approximately 3 mm deep. A solvent based adhesive, such as Duall-88, is preferably used to secure components of the finished insole together. The finished insoles 22 are assembled and sent to the foot practitioner or other footwear provider for fitting to the person.

Figure 19:
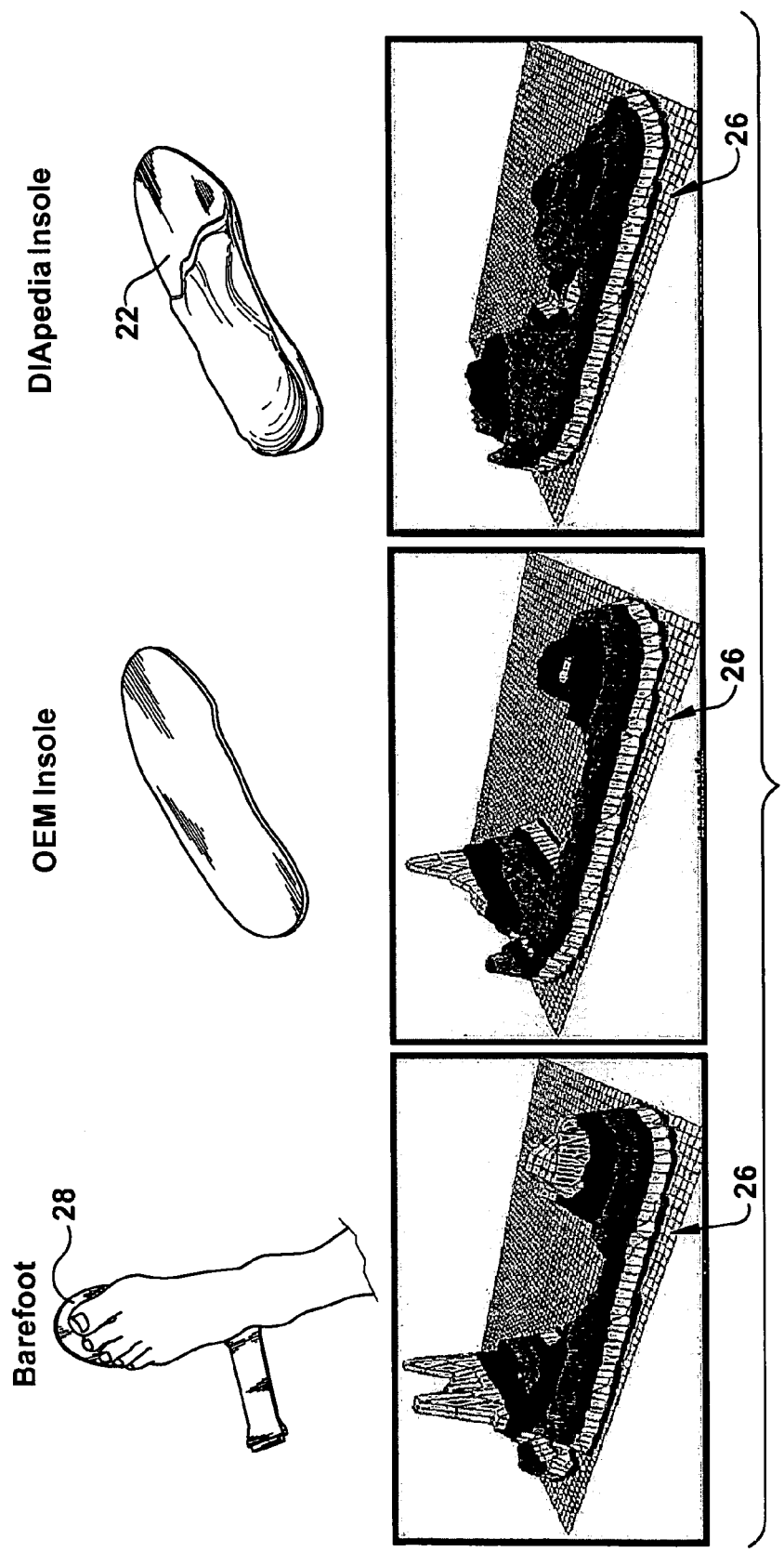
FIG. 19 illustrates the plantar pressure distributions measured during validation comparison of the indicated barefoot insole, OEM insole and the present improved pressure reducing insole, graphically illustrates the reductions in plantar pressure obtained using the improved insole of the present application.

FIG. 19 graphically illustrates the plantar pressure distributions 26 measured during validation comparison testing for each of the indicated barefoot insole, OEM insole and the improved pressure reducing insole of the present application, where the graphic data in the shape of a foot pressure is thickest where the pressures are highest. Obviously, the improved insole 22 of this application created a reduced pressure condition over the barefoot and original equipment manufacturers (OEM) insole scenarios.

While the present improved methods, processes, system and insole have been described herein in connection with one or more embodiments, it is understood that it should not be limited in any way, shape or form to any specific embodiment but rather constructed in broad scope and breadth in accordance with the recitation of the following claims.

We claim:

1. A method for the production of pressure reducing insoles for a person, comprising the steps of:
   a. measuring the three dimensional shape of a foot of a person being measured for a pressure reducing insole,
   b. selecting a predetermined insole having an outline which best corresponds to the measured shape of a foot of a person being measured,
   c. aligning the measured shape of a foot outline with the selected predetermined insole outline,
   d. measuring the distribution of plantar pressures applied by a person being measured for a pressure reducing insole,
   e. generating a foot display which combines, orients and aligns the measured shape of a foot and the distribution of plantar pressures applied by a person being measured,
   f. identifying a region within the distribution of plantar pressures on the foot display where necessary changes are to be located in the pressure reducing insole to reduce elevated plantar pressure,
   g. generating a three dimensional insole display which combines and aligns the foot display having the insole outline, the identified region within the distribution of plantar pressure and the three dimensional shape of a foot of a person being measured, and
   h. modifying the pressure reducing insole by creating an intervention relative to a shape of the pre-measured plantar pressure distribution.

2. The method of claim 1 wherein the step of modifying the pressure reducing insole by creating an intervention further includes creating a relief directly under the identified region within the distribution of plantar pressure applied to the insole.

3. The method of claim 2 further including the step of adding to the relief a resilient, flexible elastomeric material preferably of a hardness of between approximately 1–10 Shore A durometer.

4. The method of claim 1 wherein the pressure reducing insole is an ethylene vinyl acetate foam material, having a hardness of between 15–60 Shore A durometer and a thickness of between approximately 5 to 25 mm.

5. The method of claim 1 wherein the step of modifying the pressure reducing insole by creating an intervention further includes creating an elevation at a location adjacent to an identified region within the distribution of plantar pressures applied to the insole.

6. The method of claim 1 wherein the step of modifying the pressure reducing insole by creating an intervention further includes creating an elevation at a location distant from an identified region within the distribution of plantar pressures applied to the insole.

7. The method of claim 1 wherein the step of modifying the predetermined pressure reducing insole by creating an intervention includes creating at least one relief or at least one elevation relative to the distribution of plantar pressure applied to the insole.

8. The method of claim 1 wherein the step of modifying the predetermined pressure reducing insole by creating an intervention includes creating at least one relief and at least one elevation relative to the distribution of plantar pressure applied to the insole.

9. A method for the production of pressure reducing insoles for a person, comprising the steps of:

a. measuring the three dimensional shape of a foot of a person being measured for a pressure reducing insole,
b. selecting a predetermined insole having an outline which best corresponds to the measured shape of a foot of a person being measured,
c. aligning the measured shape of a foot outline with the selected predetermined insole outline,
d. measuring the distribution of plantar pressures applied by a person being measured for a pressure reducing insole,
e. generating a foot display which combines, orients and aligns the measured shape of a foot and the distribution of plantar pressures applied by a person being measured,
f. identifying a region within the distribution of plantar pressures on the foot display where necessary changes are to be located in the pressure reducing insole to reduce elevated plantar pressure,
g. generating a three dimensional insole display which combines and aligns the foot display having the insole outline, the identified region within the distribution of plantar pressure and the three dimensional shape of a foot of a person being measured, and
h. generating the pressure reducing insole of two layers of material, a base layer of foam material having a durometer of between 15–60 Shore A hardness, and a covering layer of material having a durometer of between 5–55 Shore A hardness.

10. The method of claim 9 further including the step of modifying the predetermined pressure reducing insole by creating an intervention relative to a shape of a plantar pressure distribution to be reduced within said base layer and an identified region within the distribution of plantar pressure applied to the insole.

11. The method of claim 10 wherein said step of creating an intervention comprises creating a relief including adding resilient, flexible elastomeric material to the relief.

12. The method of claim 9 wherein the base layer is between 3–25 mm thick.

13. The method of claim 9 wherein the covering layer is less than 5 mm thick.

14. A method for production of pressure reducing insoles for a person, comprising the steps of:
a. measuring the three dimensional shape of a foot of a person being measured for a pressure reducing insole,
b. selecting a predetermined insole having an outline which best corresponds to the measured projected two dimensional shape of a foot of a person being measured,
c. aligning the measured shape of a foot with the selected predetermined insole outline,
d. measuring the distribution of plantar pressures applied by a person being measured for a pressure reducing insole,
e. generating a foot display which combines, orients and aligns the measured shape of a foot and the distribution of plantar pressures applied by a person being measured,
f. identifying a region within the distribution of plantar pressures on the foot display where necessary changes are to be located in the pressure reducing insole to reduce elevated plantar pressure, and
g. generating a three dimensional insole display which combines and aligns the two dimensional display having the insole outline, the identified region within the distribution of plantar pressure, and the three dimensional shape of a foot of a person being measured, and
h. modifying the insole by creating an intervention formed relative to a threshold pressure contour line based upon the identified region within the distribution of plantar pressure applied to the insole.

15. A system for manufacturing a custom pressure reducing insole for a person, said system comprising;
a) means for a foot practitioner to measure and electronically store the distribution of plantar pressures applied by a person being measured for a pressure reducing insole,
b) means for a foot practitioner to measure and electronically store the three dimensional shape of a foot of a person being measured for a pressure reducing insole,
c) means for a foot practitioner to communicate the electronically stored distribution of plantar pressures and three dimensional shape of a foot of a person being measured for a pressure reducing insole to a manufacturing facility,
d) an electronically stored two dimensional outline of a predetermined insole which best corresponds to an outline of the measured and stored shape of a foot of a person being measured,
e) processing means at a manufacturing facility for generating and storing an electronic foot display which combines and aligns two sets of stored data from a foot practitioner: 1) the three dimensional shape of a foot of a person being measured, and 2) the measured distribution of plantar pressures applied by a person being measured, with the stored two dimensional outline of an insole,
f) said processing means also generating a three dimensional insole display which combines and aligns the foot display having the, measured foot shape and plantar pressure distribution of a person being measured, with the stored insole outline,
g) said processing means also identifying at least one region of the insole display based upon the measured distribution of plantar pressures where changes are to be made to an insole to reduce elevated plantar pressure,
h) manufacturing means at a manufacturing facility for receiving instructions from said processing means and modifying an insole along the identified region, and
i) basing said at least one identified region of the insole display on predetermined threshold pressure contour lines.

16. The system of claim 15 wherein the predetermined threshold pressure contour lines are above approximately 200 kPa.

* * * * *